United States Patent [19]

Taguchi

[11] Patent Number: 5,528,359
[45] Date of Patent: Jun. 18, 1996

[54] IMAGE SCANNING APPARATUS AND METHOD

[75] Inventor: Hiromichi Taguchi, Kanagawa, Japan

[73] Assignee: Sony Corporation, Tokyo, Japan

[21] Appl. No.: 279,873

[22] Filed: Jul. 25, 1994

[30] Foreign Application Priority Data

Jul. 30, 1993 [JP] Japan ..................... 5-208766

[51] Int. Cl.⁶ .................................................. G01B 11/00
[52] U.S. Cl. .......................... 356/237; 356/241; 356/378
[58] Field of Search .................................. 356/241, 237, 356/378, 384

[56] References Cited

U.S. PATENT DOCUMENTS

| | | | |
|---|---|---|---|
| 3,806,252 | 4/1974 | Harris et al. | 356/378 |
| 3,873,211 | 3/1975 | Watson | 356/378 |
| 4,687,328 | 8/1987 | Shiraishi et al. | 356/378 |
| 4,930,889 | 6/1990 | Van Donselaar et al. | 356/384 |

FOREIGN PATENT DOCUMENTS

159701  7/1988  Japan ..................... 356/364

Primary Examiner—Richard A. Rosenberger
Attorney, Agent, or Firm—Ronald P. Kananen

[57] ABSTRACT

An image scanning apparatus and method for automatically inspecting a product having light transmission regions, so as to detect any defect therein with accuracy and rapidity. The image scanning method inspects the product by disposing a light source on one side of the product and an optical sensor on the other side thereof, varying the incidence angle of a light output emitted from the light source to the light transmission regions of the product, then receiving, by the optical sensor, the light transmitted through the light transmission regions at each of the varied incidence angles, thereby acquiring image data with regard to the product, and detecting any defect in the product on the basis of the image data thus obtained at the incidence angles. The image scanning apparatus comprises a light source disposed on one side of the product to be inspected, an optical sensor disposed on the other side thereof, a means for varying the incidence angle of a light output emitted from the light source to the light transmission regions of the product, and a means for processing the image data obtained with regard to the product at each of the varied incidence angles.

13 Claims, 6 Drawing Sheets

1 SLOT

IMAGE SCANNING APPARATUS AND METHOD

BACKGROUND OF THE INVENTION

1. Field of the Invention

The present invention relates to an image scanning method for automatically inspecting a product having light transmission regions, and an image scanning apparatus adapted to carry out such a method.

2. Description of the Related Art

Figure 1A:
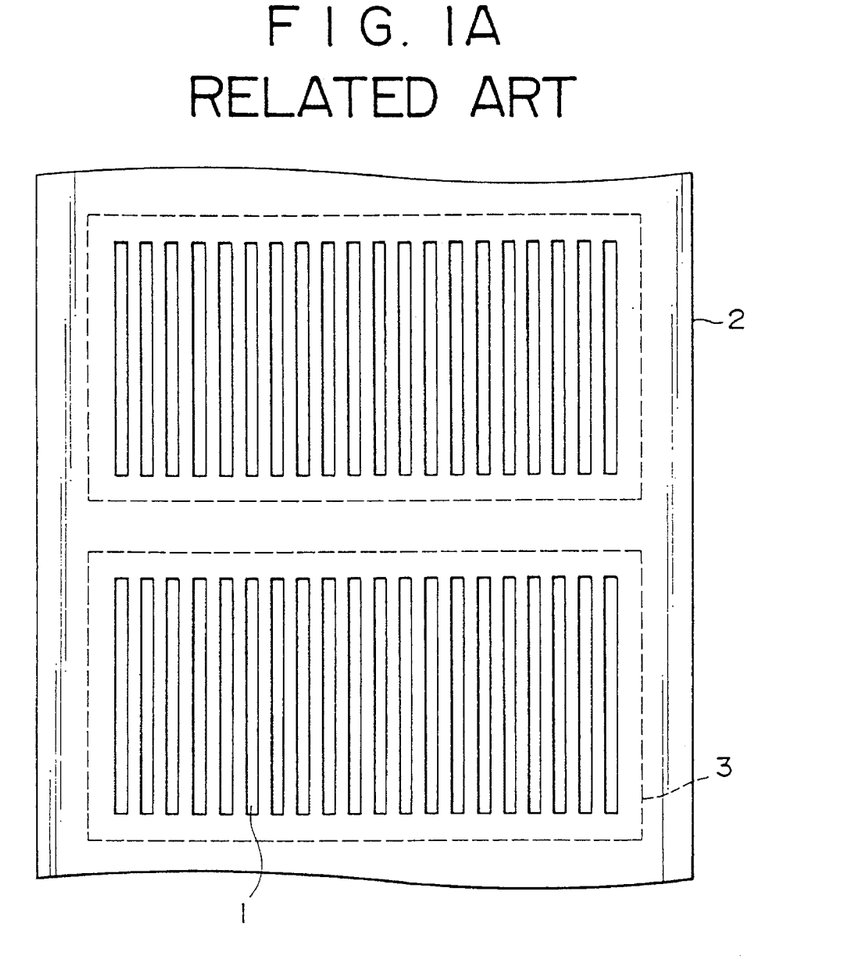
FIGS. 1A and 1B are a schematic partial plan view and a partial sectional view of an aperture grille in the related art.
Figure 1B:
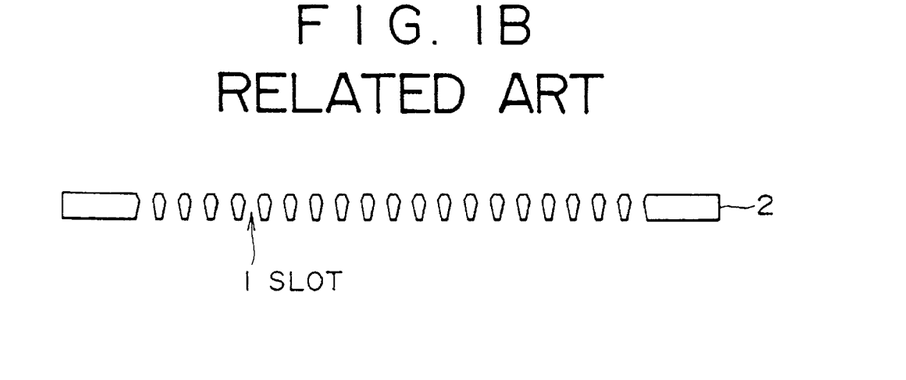

An aperture grille, which is a color selecting mechanism used in, e.g., a picture tube known as Trinitron (trade name), is generally produced as illustrated in a schematic partial plan view of FIG. 1A and a partially enlarged longitudinal sectional view of FIG. 1B, wherein a band-shaped thin metal plate is etched successively like a blind to form slots 1 therein, and then it is finished to have a predetermined size. In FIG. 1A, a contour 3 of the aperture grille is denoted by a broken line.

It has been generally customary heretofore that whether the shape of the slots 1 in the aperture grille is within a standard range or not is decided by visual inspection or by measuring the transmittance of parallel light rays transmitted through the slots 1.

According to such a conventional inspection method, however, it is impossible to detect any small defects in the slots 1, although great defects may be detectable properly. Further, detection of any defect in the sectional shape of the aperture grille is extremely difficult.

There may be contrived another method for detection of defects in the slots 1 of the aperture grille by setting a light source and a camera fixedly, then passing the aperture grille through the space formed between the light source and the camera, and photographing the slots 1 of the aperture grille by the camera to thereby detect any defects. However, according to this method also, it is still difficult to find the defects since the amount of image data obtained by the camera is insufficient. And it is nearly impossible to detect any defective portion particularly in the sectional shape of the aperture grille.

OBJECT AND SUMMARY OF THE INVENTION

It is therefore an object of the present invention to provide an automatic image scanning method and an apparatus adapted to carry out the same, which are both capable of automatically inspecting any defect with accuracy and rapidity in a product having light transmission regions, such as an aperture grille, particularly any defect in the sectional shape thereof.

The object mentioned above is achievable by an improved image scanning method of the present invention which automatically inspects a product having light transmission regions, by disposing a light source on one side of the product while disposing an optical sensor on the other side thereof, subsequently varying the incidence angle of a light output which is emitted from the light source and is incident upon the light transmission regions of the product, then receiving, by the optical sensor, the light transmitted through the light transmission regions of the product at each of the varied incidence angles and, after acquiring the image data relative to the product, detecting the defect of the product on the basis of the image data obtained at each incidence angle.

In the automatic image scanning method of the present invention, the light source is relatively displaceable to the light transmission regions of the product so as to vary the incidence angle of the light output emitted from the light source and caused to be incident upon the light transmission regions of the product. And the optical sensor is also displaceable in compliance with the relative displacement of the light source to the light transmission regions of the product being inspected. The optical sensor may consist of a single one-dimensional line sensor, or a plurality of one-dimensional line sensors or a two-dimensional line sensor.

For the purpose of achieving the object mentioned above, an image scanning apparatus according to one aspect of the present invention for automatically inspecting a product having light transmission regions comprises: (a) a light source disposed on one side of the product to be inspected; (b) an optical sensor disposed on the other side of the product; (c) an incidence angle varying means for varying the incidence angle of a light output emitted from the light source and caused to be incident upon the light transmission regions of the product; and (d) an image data processing means for processing the image data obtained with regard to the product by the optical sensor which has received the light transmitted through the light transmission regions of the product at each of the varied incidence angles.

In the above image scanning apparatus of the present invention, the incidence angle varying means may be formed into a light source moving mechanism which displaces the light source relatively to the light transmission regions of the product to be inspected. And a sensor moving mechanism may be provided for displacing the optical sensor in compliance with the relative displacement of the light source to the light transmission regions of the product being inspected.

Further for the purpose of achieving the object mentioned, an image scanning apparatus according to another aspect of the invention for automatically inspecting a product having light transmission regions comprises: (a) a plurality of light sources disposed on one side of the product and emitting light outputs thereof at mutually different incidence angles to the light transmission regions of the product; (b) an optical sensor disposed on the other side of the product; and (c) an image data processing means for processing the image data obtained with regard to the product by the optical sensor which has received the light transmitted through the light transmission regions of the product at each of the different incidence angles.

In any of the above image scanning apparatus of the invention, the optical sensor may consist of a single one-dimensional line sensor, or a plurality of one-dimensional line sensor or a two-dimensional line sensor.

Figure 2A:
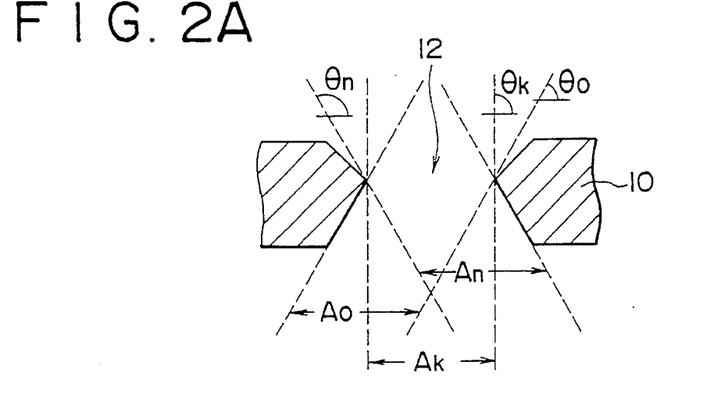
FIGS. 2A to 2C are schematic sectional views of a product, which is to be inspected, for explaining the principle of an automatic image scanning method of the present invention.
Figure 2B:
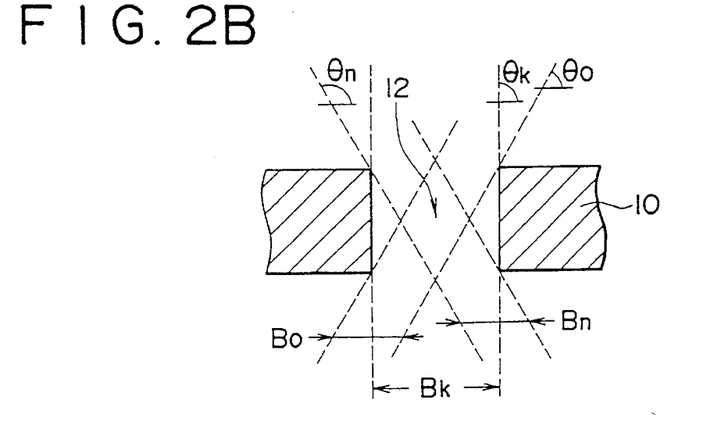
Figure 2C:
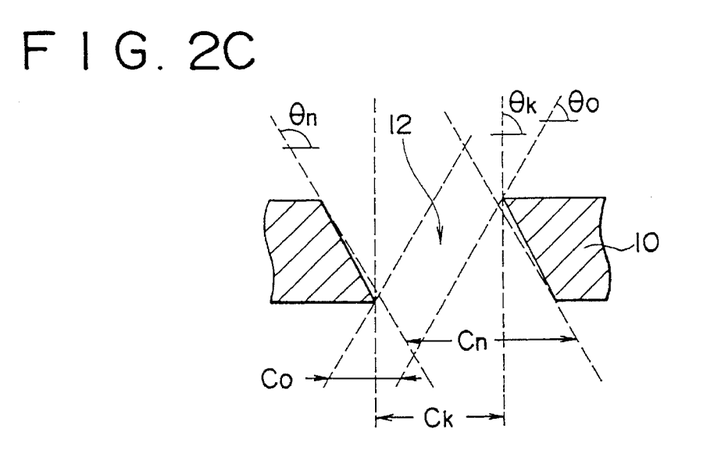

Suppose now that a schematic sectional shape of a product 10 shown in FIG. 2A is normal, and sectional shapes thereof shown in FIGS. 2B and 2C are abnormal. Under such conditions, when a light output from a light source is incident upon a light transmission region 12 of the product 10 at a certain incidence angle θk, the image data (represented for convenience by arrows Ak, Bk and Ck in FIGS. 2A, 2B and 2C) are assumed here to be the same. However, when the light output from the light source is incident upon the light transmission region 12 of the product 10 at certain incidence angles θ0 and θn, the resultant image data (represented for convenience by arrows A0, An, B0, Bn, C0 and Cn in FIGS. 2A, 2B and 2C) are different from one another.

Therefore, it is nearly impossible to detect any defect in the sectional shape of the product by the known method which passes the product through a space formed between a light source and a camera disposed fixedly, and photographs the light transmission regions of the product by the camera while setting the incidence angle θk of the light output from the light source to the product to thereby detect any defect of the light transmission regions.

However, according to the present invention, the light transmission region of the product is irradiated with the light outputs of mutually different incidence angles a plurality of times to consequently obtain a plurality of image data relative to the product viewed at different angles. And a required process is executed on the basis of such a plurality of image data, thereby discriminating the difference among the sectional shapes shown in FIGS. 2A, 2B and 2C. Therefore it becomes possible to attain a high precision in inspecting the shape of the light transmission regions or the sectional shape of the product.

The above and other features and advantages of the present invention will become apparent from the following description which will be given with reference to the illustrative accompanying drawings.

DETAILED DESCRIPTION OF THE PREFERRED EMBODIMENTS

Hereinafter the present invention will be described in detail with reference to preferred embodiments thereof shown in the accompanying drawings. The image scanning apparatus of the invention is adapted for automatically inspecting a product (e.g., aperture grille) having light transmission regions (e.g., slots). The first and second preferred embodiments represent the image scanning apparatus according to one aspect of the present invention, and the third preferred embodiment represents the image scanning apparatus according to another aspect of the invention.

Now the first embodiment representing the image scanning apparatus of the invention will be described below in detail.

In the image scanning apparatus of the first embodiment shown schematically in FIG. 3, an incidence angle varying means is a light source moving mechanism which displaces a light source 20 to light transmission regions 12 of a product 10 to be inspected. An optical sensor 30 consists of a single one-dimensional line sensor. And there is provided a sensor moving mechanism 32 which displaces the optical sensor 30 in compliance with the relative displacement of the light source 20 to the light transmission regions 12 of the product 10. The required number of sensing elements in the one-dimensional line sensor may be at least equal to the number of the light transmission regions 12 to be inspected, but may preferably be three times or so the number of the regions 12. And the lengths of the light source 20 and the optical sensor 30 need to cover the whole light transmission regions 12 in the transverse direction of the product 10.

Figure 3A:
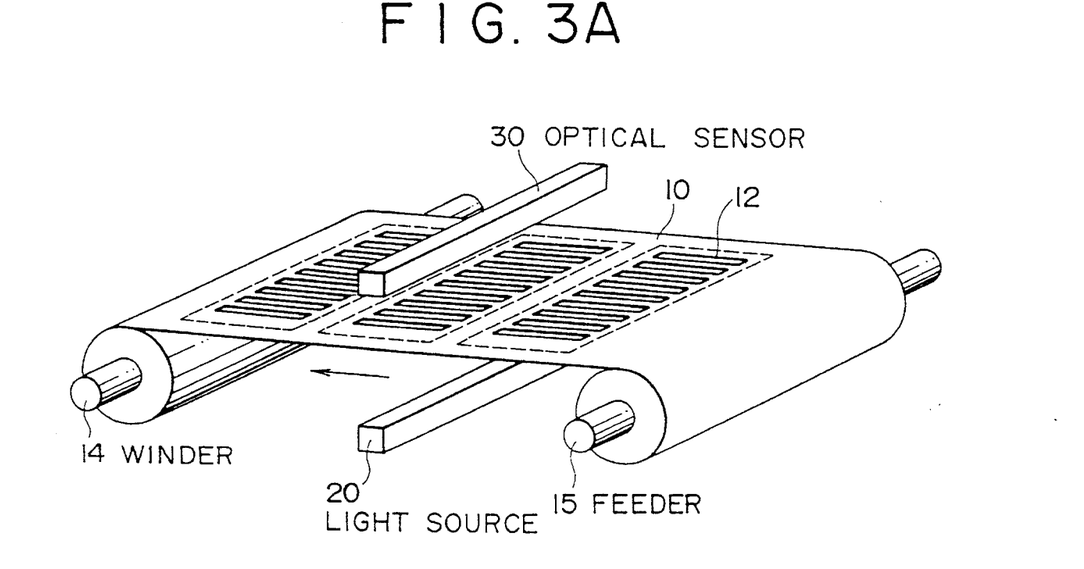
FIGS. 3A and 3B are schematic diagrams illustrating the positional relationship between a product to be inspected and an automatic image scanning apparatus in a first embodiment of the invention.

FIG. 3A schematically illustrates the positional relationship between the band-shaped elongate product 10 and the automatic image scanning apparatus. In the product 10, there is formed an aperture grille which is a color selecting mechanism employed in a cathode-ray tube. More specifically, light transmission regions 12 are formed in the product 10 by successively etching the same in the shape of a blind. The product 10 wound around a feeder 15 is forwarded therefrom in the direction of an arrow in FIG. 3A while being repeatedly advanced and stopped so as to be inspected, and then is taken up by a winder 14 after completion of the inspection. The inspection of the light transmission regions 12 is performed automatically during each stop of the product 10. In this case, the direction of displacement of the product 10 is termed a longitudinal direction thereof, and the direction orthogonal to the longitudinal direction is termed a transverse direction. In the first embodiment, the light transmission regions 12 are striped slots extending in the longitudinal direction.

The light source 20 is disposed on one side of the product 10, while the optical sensor 30 consisting of a single one-dimensional line sensor is disposed on the other side of the product 10. The light source 20 and the optical sensor 30 are positioned linearly in the transverse direction of the product 10.

Figure 3B:
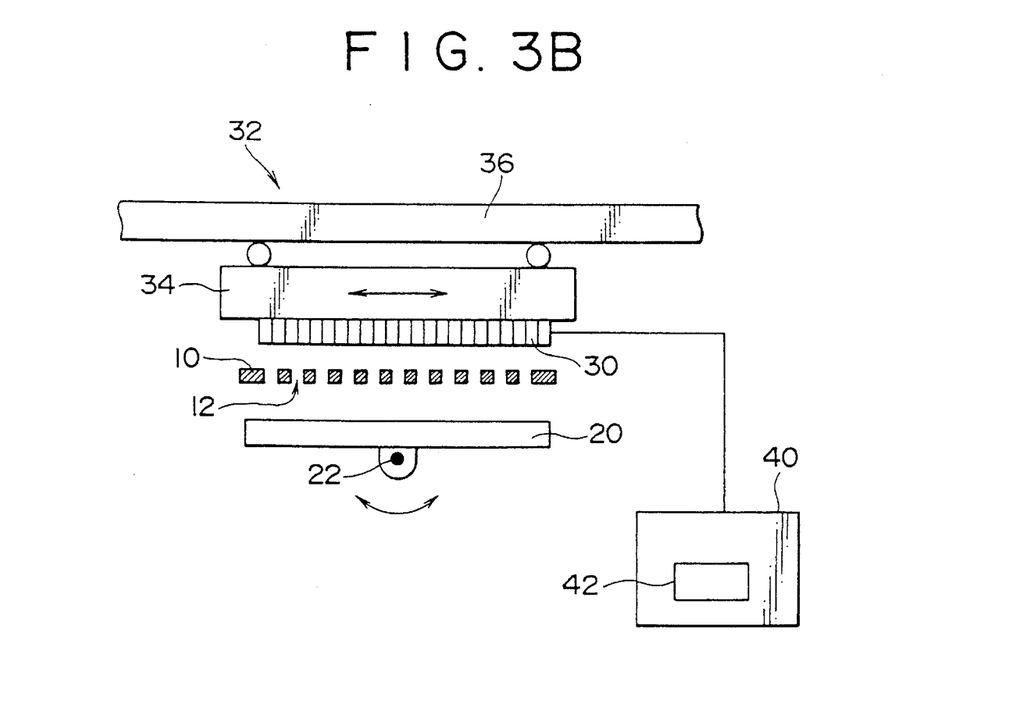

It is preferred that the light source 20 consists of an aggregate of spot light sources which are capable of emitting parallel light rays. And desirably the light source 20 is equipped with a louver. The incidence angle varying means is a light source moving mechanism which displaces the light source 20 relatively to the light transmission regions 12 of the product 10. More concretely, the incidence angle varying means in the first embodiment comprises an unshown combination of a motor and gears for rotating the light source 20 around an axis 22 perpendicular to the drawing paper face of FIG. 3, as illustrated in FIG. 3B. The incidence angle of the light emitted from the light source 20 to the light transmission region 12 is varied in accordance with the rotation of the light source 20.

The optical sensor 30 is attached to the sensor moving mechanism 32 as schematically illustrated in FIG. 3B. The sensor moving mechanism 32 comprises, for example, a support base 34 for mounting the optical sensor 30 thereon, a rail 36, and a support-base shifter (not shown) such as an air cylinder or a combination of a motor and gears. The optical sensor 30 can be displaced in compliance with a displacement of the support base 34 on the rail 36 effected by the support base shifter.

Figure 4A:
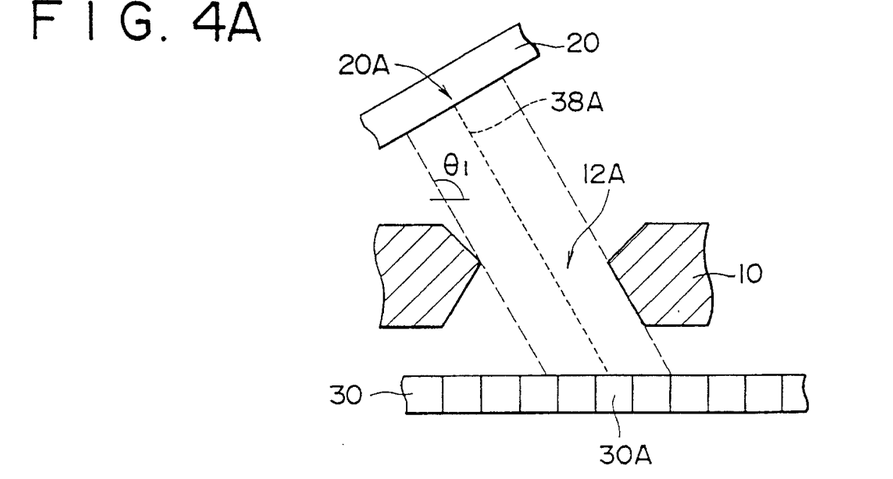
FIGS. 4A to 4C are schematic sectional views of a product, which is to be inspected and has light transmission regions, for explaining an automatic image scanning method employing the image scanning apparatus of the first embodiment.
Figure 4B:
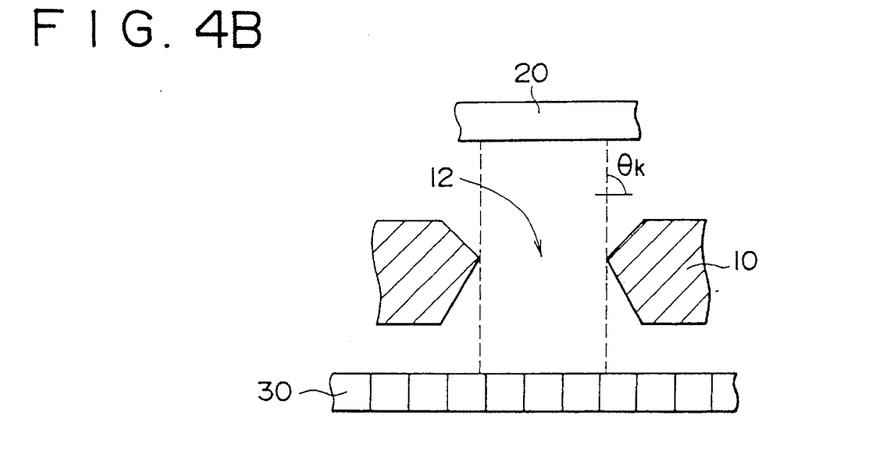
Figure 4C:
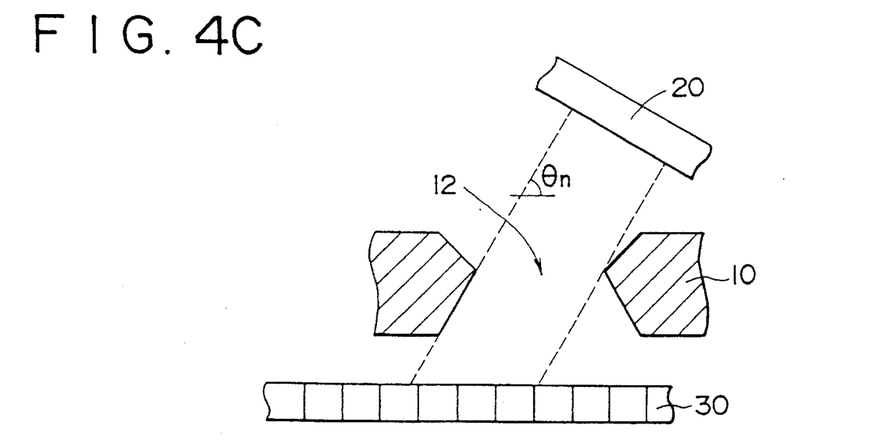

The optical sensor 30 is moved in compliance with a displacement of the light source 20 relative to the light transmission regions 12 of the product 10. The relationship between the displacement state of the light source 20 by the incidence angle varying means and the displacement state of the optical sensor 30 by the sensor moving mechanism 32 is illustrated in FIG. 4A which includes a schematic sectional view of the product 10. In the first embodiment, the light source 20 and the optical sensor 30 are so disposed that one predetermined portion 20A of the light source 20 and one predetermined sensor element 30A of the optical sensor 30 are exactly positioned on an axis 38A which passes through one predetermined light transmission region 12A. The light source 20 and the optical sensor 30 are displaced relatively to each other. FIGS. 4A to 4C will be described later in detail.

The automatic image scanning apparatus of the first embodiment is further equipped with an image data processing means 40. The optical sensor 30 receives the light outputs of various incidence angles transmitted through the light transmission regions 12 of the product 10. And the image data processing means 40 executes its process on the basis of the image data thus obtained with regard to the product 10 at each of the incidence angles. In the concrete, the image data process includes, for example, calculations of adding, differentiating and weighting a plurality of the image data obtained. The edges of the light transmission regions 12 can be recognized by differentiating the light intensity distribution in the image data. Also the center of the light transmission regions 12 can be calculated by first finding the light intensity distribution from the relationship of the light intensities in the image data and then calculating the position of the areal gravity center of the light intensity distribution. The image data processing means 40 is equipped with a display device 42 such as a CRT so as to display the result of the image data process or the result of the inspection.

Hereinafter an image scanning method adopting the apparatus of the first embodiment for automatic inspection of a product having light transmission regions will be described with reference to FIGS. 4A to 4C which are schematic sectional views of the product 10 to be inspected.

As illustrated in FIG. 3, the product 10 wound around the feeder 15 is forwarded therefrom in the direction of an arrow while being advanced and stopped repeatedly. And an inspection of the light transmission regions 12 is performed automatically during each stop of the product 10. First the product 10 being advanced is brought to a stop, and a light output emitted from the light source 20 is caused to be incident upon the light transmission regions 12 of the product 10 at a preset incidence angle $\theta 1$ (FIG. 4A). For convenience, the positional state of the light source 20 and the optical sensor 30 in this stage of the operation is termed an initial positional state. The light transmitted through the light transmission regions 12 of the product 10 is received by the optical sensor 30. The one-dimensional image data obtained with regard to the product 10 at the incidence angle $\theta 1$ is supplied to the image data processing means 40 and then is stored in a memory or the like incorporated in the image data processing means 40.

Subsequently, while the product 10 is kept at a stop, the light source 20 is displaced (rotated) relatively to the light transmission regions 12 of the product 10 by the incidence angle varying means. And simultaneously therewith, the optical sensor 30 is also displaced by the sensor moving mechanism 32 in compliance with the relative displacement of the light source 20 to the light transmission regions 12. Thereafter the light output from the light source 20 is caused to be incident upon the light transmission regions 12 of the product 10 at a preset incidence angle $\theta 2$. Then the light transmitted through the light transmission regions 12 of the product 10 is received by the optical sensor 30. The one-dimensional image data obtained with regard to the product 10 at the incidence angle $\theta 2$ is supplied also to the image data processing means 40 and then is stored in the memory or the like incorporated in the image data processing means 40.

Further during the stop of the product 10, the above procedure, which includes the operations of relatively displacing the light source 20 by the incidence angle varying means, displacing the optical sensor 30 by the sensor moving mechanism 32, acquiring the image data with regard to the product 10 at the preset incidence angle $\theta (= \theta 3, \ldots, \theta k, \ldots, \theta n)$ and storing the image data in the memory in the image data processing means 40, is repeated n times (e.g., 10 times) in total. FIGS. 4B and 4C illustrate the states where the light output from the light source 20 is incident upon the light transmission regions 12 of the product 10 at the incidence angles $\theta k$ and $\theta n$ respectively in the kth and nth operations.

In this manner, a plurality (e.g., n=10) of one-dimensional image data are obtained at the mutually different incidence angles $\theta$ of the light with regard to the product 10 in the transverse direction thereof. In other words, there can be acquired a plurality of one-dimensional image data of the product 10 as viewed from various different angles in the transverse direction.

Upon completion of acquiring the image data a desired number of times (n times), the product 10 is displaced by a predetermined distance in the direction indicated by an arrow in FIG. 3A, and simultaneously the light source 20 and the optical sensor 30 are displaced respectively by the incidence angle varying means and the sensor moving mechanism 32, so that the light source 20 and the optical sensor 30 are placed in the initial positional state thereof. And the above procedure, which includes the operations of acquiring the image data of the product 10 at the incidence angle $\theta (=\theta 1, \ldots, \theta k, \ldots, \theta n)$ and storing the image data in the memory incorporated in the image data processing means 40, is repeated n times (e.g., 10 times) in total. And further such procedure is sequentially repeated in the longitudinal direction of the product 10.

Upon completion of inspecting the product of a desired length (i.e., after plural transverse inspections of the product) or upon completion of one transverse inspection of the product, a required process is executed by the image data processing means 40 on the basis of the image data obtained at each of the incidence angles and stored in the memory of the image data processing means 40, whereby any defect in the product is detected.

For such detection, a required process is executed by, e.g., adding, differentiating or weighting the plural image data thus acquired. More specifically, the image data obtained at the individual incidence angles in one transverse inspection are added to obtain composite image data. Then the light distribution intensities in such composite image data are differentiated to recognize the edges of the light transmission regions 12. When any distortion is existent in the image data corresponding to the edges of the light transmission regions thus obtained in the longitudinal direction of such regions, i.e., when the data are lacking in the requisite linearity for example, it signifies that some defects such as missing portions or irregularities are existent in the edges of the light transmission regions 12.

The center of the light transmission region 12 can be found by first obtaining the light intensity distribution from the composite image data and then calculating the position of the areal gravity center of the light intensity distribution. If the line that connects the centers of the light transmission regions 12 in the longitudinal direction lacks in the requisite linearity, it signifies that the product being inspected is defective due to nonexistence of the linearity.

Figure 5:
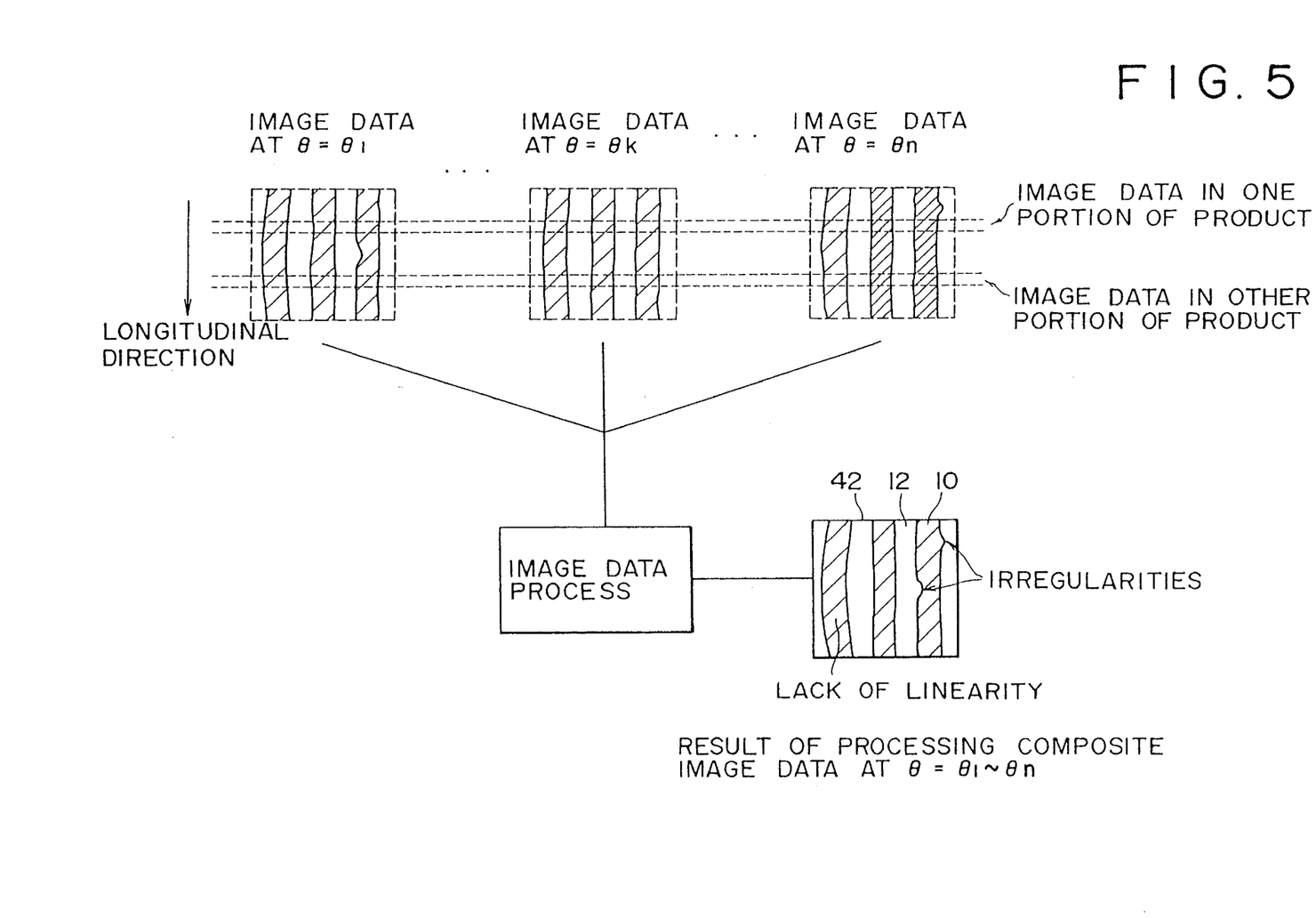
FIG. 5 is a schematic diagram showing the results of the image data process and the inspection executed in the first embodiment.

The results of the image data process and the inspection are displayed, as illustrated in FIG. 5, on a display device 42 such as a CRT provided in the image data processing means 40. FIG. 5 conceptually shows the image data acquired in the longitudinal direction of the product 10 at each of the incidence angles and also the results of processing the plural image data by adding, differentiating or weighting the same. It is possible to discriminate between the presence and the absence of any defect in the product by comparing such results of the processed image data with a preset defect discrimination reference.

Even if none of great defects is recognized in the image data obtained at the incidence angle $\theta=\theta k$ for example, it is possible, according to the result of processing the image data, to achieve exact detection of any defect such as lack of the requisite linearity or the existence of some irregularities in the product, as shown in FIG. 5.

Now a description will be given on a second embodiment which represents the automatic image scanning apparatus of the present invention.

Figure 6:
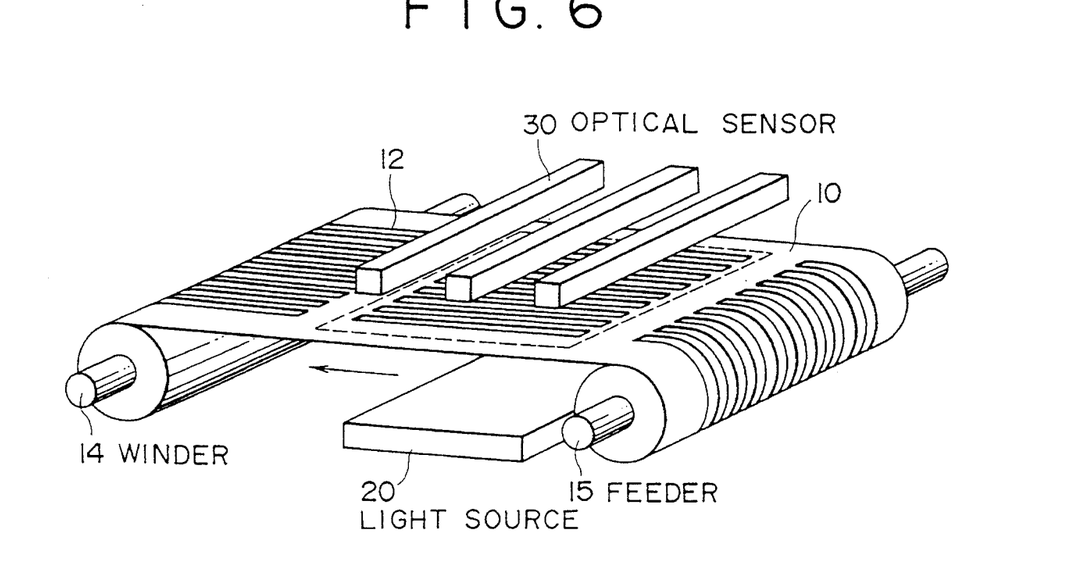
FIG. 6 is a schematic diagram illustrating the positional relationship between a product to be inspected and an automatic image scanning apparatus in a second embodiment of the invention.

Also in the image scanning apparatus of FIG. 6 according to the second embodiment which relates to the first aspect of the invention, an incidence angle varying means is a light source moving mechanism for displacing a light source 20 relatively to light transmission regions 12 of a product 10 to be inspected, as in the aforementioned first embodiment. Preferably, the light source 20 consists of a two-dimensional aggregate of spot light sources capable of emitting parallel light outputs, or consists of a surface light source. It is also desirable that the light source 20 is equipped with a louver.

As illustrated in FIG. 6, an optical sensor 30 consists of a plurality of one-dimensional line sensors arranged in the longitudinal direction. And a sensor moving mechanism is provided for displacing the optical sensor 30 in compliance with the relative displacement of the light source 20 to the light transmission regions of the product 10. The number of the one-dimensional line sensors may be selectively determined in accordance with the size of the product 10 to be inspected. In the example of FIG. 6, three one-dimensional line sensors are depicted. The lengths of the light source 20 and the optical sensor 30 need to cover the whole light transmission regions 12 in the transverse direction of the product 10. With the exception that the optical sensor 30 consists of a plurality of one-dimensional line sensors, the image scanning apparatus of the second embodiment may be the same in construction as the aforementioned apparatus of the first embodiment, and therefore a detailed explanation thereof is omitted here.

Hereinafter a description will be given on an image scanning method which adopts the apparatus of the second embodiment for automatically inspecting a product having light transmission regions.

As illustrated in FIG. 6, the product 10 wound around the feeder 15 is forwarded in the direction of an arrow while being advanced and stopped repeatedly. And automatic inspection of the light transmission regions 12 is performed during a stop of the product 10. First the product 10 being advanced is brought to a stop and, after the light source 20 and the optical sensor 30 are both placed in the initial positional state thereof, a light output from the light source 20 is caused to be incident upon the light transmission regions 12 of the product 10 at a preset incidence angle $\theta 1$. Then the light transmitted through the light transmission regions 12 of the product 10 is received by the optical sensor 30 which consists of a plurality of one-dimensional line sensors. The resultant two-dimensional image data obtained with regard to the product 10 at the incidence angle $\theta 1$ are supplied to an image data processing means 40 and then is stored in a memory or the like incorporated in the image data processing means 40.

Subsequently, while the product 10 is kept at a stop, the light source 20 is displaced (rotated) relatively to the light transmission regions 12 of the product 10 by the incidence angle varying means. And simultaneously therewith, the optical sensor 30 is also displaced by the sensor moving mechanism 32 in compliance with the relative displacement of the light source 20 to the light transmission regions 12.

Thereafter the light output from the light source 20 is caused to be incident upon the light transmission regions 12 of the product 10 at a preset incidence angle $\theta 2$. Then the light transmitted through the light transmission regions 12 of the product 10 is received by the optical sensor 30. The two-dimensional image data obtained with regard to the product 10 at the incidence angle $\theta 2$ is supplied also to the image data processing means 40 and then is stored in the memory or the like incorporated in the image data processing means 40.

Further during the stop of the product 10, the above procedure, which includes the operations of relatively displacing the light source 20 by the incidence angle varying means, displacing the optical sensor 30 by the sensor moving mechanism 32, acquiring the two-dimensional image data with regard to the product 10 at the present incidence angle $\theta$ (= $\theta 3, \ldots, \theta k, \ldots, \theta n$) and storing the image data in the memory in the image data processing means 40, is repeated n times (e.g., 10 times) in total.

In this manner, a plurality (e.g., n=10) of image data are obtained at the mutually different incidence angles $\theta$ of the light with regard to the product 10 over certain lengths in the transverse and longitudinal directions of the product 10. In other words, there can be acquired a plurality of two-dimensional image data of the product 10 as viewed from various different angles over certain lengths in the transverse and longitudinal directions of the product 10.

Upon completion of acquiring the image data a desired number of times (n times), the product 10 is displaced by a predetermined distance in the direction indicated by an arrow in FIG. 6, and simultaneously the light source 20 and the optical sensor 30 are displaced respectively by the incidence angle varying means and the sensor moving mechanism 32, so that the light source 20 and the optical sensor 30 are placed in the initial positional state thereof. And the above procedure, which includes the operations of acquiring the image data of the product 10 at the incidence angle $\theta$ (=$\theta 1, \ldots, \theta k, \ldots, \theta n$) and storing the image data in the memory incorporated in the image data processing means 40, is repeated n times (e.g., 10 times) in total. And further such procedure is sequentially repeated in the longitudinal direction of the product 10.

Upon completion of inspecting the product 10 of a desired length (i.e., after plural transverse inspections of the product) or upon completion of one transverse inspection of the product, a required process is executed by the image data processing means 40 as in the aforementioned first embodiment on the basis of the image data obtained at each of the incidence angles and stored in the memory of the image data processing means 40, whereby any defect in the product is detected.

The results of the image data process and the inspection are displayed, in the same manner illustrated in FIG. 5, on a display device 42 such as a CRT provided in the image data processing means 40. It is possible to discriminate between the presence and the absence of any defect in the product by comparing such results of the processed image data with a preset defect discrimination reference.

In the image scanning apparatus of the second embodiment where the optical sensor consists of a plurality of one-dimensional line sensors, inspection of the product can be performed more efficiently than in the foregoing apparatus of the first embodiment.

It is to be noted that the optical sensor may consist of a two-dimensional line sensor instead of a plurality of one-dimensional line sensors. The automatic image scanning method in such a case can be carried out in the same manner as the foregoing method described in connection with the second embodiment.

Now a description will be given on a third embodiment representing the image scanning apparatus of the present invention.

Figure 7:
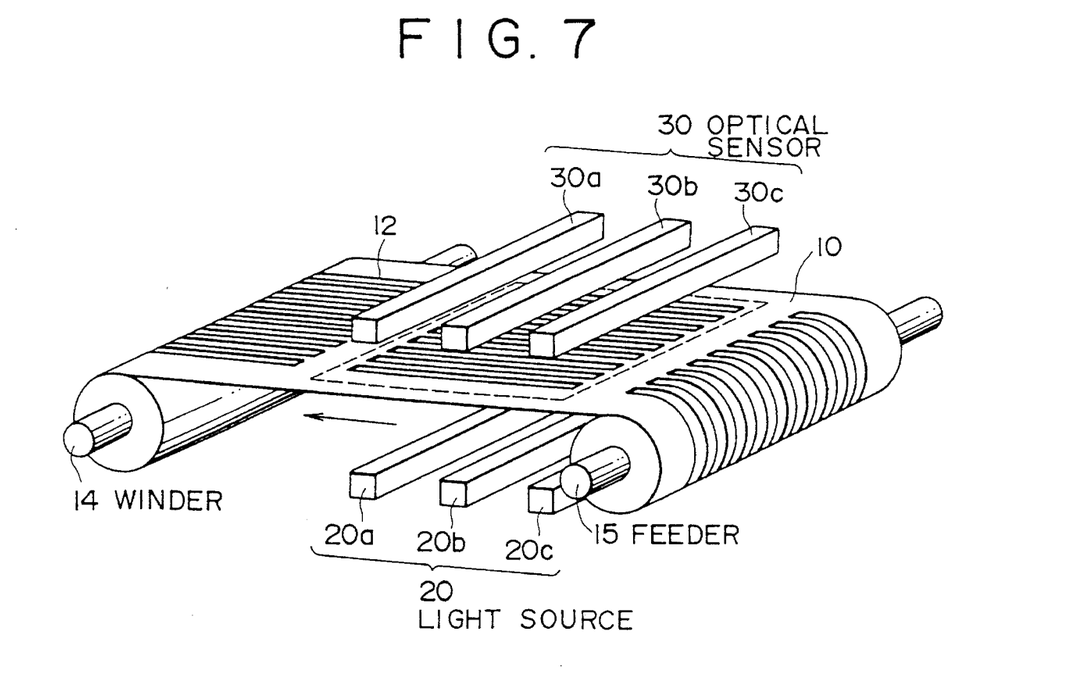
FIG. 7 is a schematic diagram illustrating the positional relationship between a product to be inspected and an automatic image scanning apparatus in a third embodiment of the invention.

In the image scanning apparatus of the third embodiment, a plurality of light sources 20 are disposed, differently from the aforementioned first or second embodiment, on one side of the product to be inspected, as illustrated in FIG. 7. The light sources 20 are so positioned that the light outputs emitted therefrom are incident upon the light transmission regions 12 of the product at mutually different angles. Each of the light sources 20 is held fixedly.

In the image scanning apparatus of the third embodiment, an optical sensor 30 is held fixedly and consists of a plurality of one-dimensional line sensors corresponding to the light sources 20 respectively. More specifically, a one-dimensional line sensor is positioned in correspondence to one light source 20. The arrangement may be so modified that the plural one-dimensional line sensors are integrated into a single structure or are arrayed at a predetermined interval or with a positional deviation in the transverse direction of the product. In case the plural one-dimensional line sensors are arrayed with a positional deviation in the transverse direction of the product, preferably the light sources and the one-dimensional line sensors corresponding thereto are so disposed that, similarly to the aforementioned example of FIG. 4A, one predetermined light source 20A and one predetermined sensor element 30A of the one-dimensional line sensor are exactly positioned on an axis 38A which passes through one predetermined light transmission region 12A.

The lengths of the light sources 20 and the optical sensor 30 need to cover the whole light transmission regions 12 in the transverse direction of the product 10 to be inspected. The light sources 20 and the optical sensor 30 are disposed linearly in the transverse direction of the product 10. The number of the light sources 20 and that of the one-dimensional line sensors constituting the optical sensor 30 may be determined properly depending on the desired number of image data to be acquired per inspection of the product. In the example of FIG. 7, there are depicted three light sources 20a, 20b, 20c and three one-dimensional line sensors 30a, 30b, 30c.

In the third embodiment also, an image data processing means is provided similarly to the first or second embodiment. The image data processing means processes the image data obtained with regard to the product from the optical sensor which receives the light transmitted through the light transmission regions of the product at each of the incidence angles.

In the image scanning apparatus of the third embodiment also, the product 10 wound around a feeder 15 is forwarded in the direction of an arrow in FIG. 7 while being advanced and stopped repeatedly, and after completion of an inspection, the product 10 is taken up by a winder 14. An inspection of the light transmission regions 12 is performed automatically during a stop of the product 10.

Hereinafter a description will be given of an image scanning method which adopts the apparatus of the third embodiment for automatically inspecting a product having light transmission regions.

As illustrated in FIG. 7, the product 10 wound around the feeder 15 is forwarded therefrom in the direction of an arrow while being advanced and stopped repeatedly. An automatic inspection of the light transmission regions 12 is performed during a stop of the product 10. First, the product 10 being advanced is brought to a stop, and a light output from the first light source 20a having a preset incidence angle $\theta1$ is caused to be incident upon the light transmission regions 12 of the product 10. Then the light transmitted through the light transmission regions 12 of the product 10 is received by the first one-dimensional sensor 30a. The resultant one-dimensional image data obtained with regard to the product 10 at the incidence angle $\theta1$ is supplied to the image data processing means 40 and then is stored in a memory or the like incorporated in the image data processing means 40.

Subsequently the product 10 is brought to a stop after being forwarded by a distance corresponding to the interval of the light sources and that of the one-dimensional line sensors, and a light output from the second light source 20b having a preset incidence angle $\theta2$ is caused to be incident upon the light transmission regions 12 of the product 10. The light transmitted through the light transmission regions 12 of the product 10 is received by the second one-dimensional line sensor 30b. The resultant one-dimensional image data obtained with regard to the product 10 at the incidence angle $\theta2$ is supplied also to the image data processing means 40 and then is stored in the memory or the like incorporated in the image data processing means 40.

Further the product 10 is forwarded again by a distance corresponding to the interval of the light sources and that of the one-dimensional line sensors. And during a stop of the product 10 subsequent to such advance, the above procedure, which includes the operations of acquiring the one-dimensional image data with regard to the product 10 by the third, fourth, ..., nth light sources (incidence angles=$\theta3$, $\theta4$, ..., $\theta n$) and the third, fourth, ..., nth one-dimensional line sensors and then storing the image data in the memory of the image data processing means 40, is repeated n times (e.g., 10 times) in total.

In this manner, a plurality (e.g., n=10) of image data are obtained at the mutually different light incidence angles $\theta$ with regard to the product 10 in the transverse direction thereof. In other words, there can be acquired a plurality of one-dimensional image data of the product 10 as viewed from various different angles in the transverse direction.

Upon completion of acquiring the image data a desired number of times (n times), the product 10 is advanced to another position, and the above procedure, which includes the operations of acquiring the one-dimensional image data of the product 10 at the incidence angles $\theta$ (=$\theta1$, ..., $\theta k$, ..., $\theta n$) and storing the image data in the memory incorporated in the image data processing means 40, is repeated n times (e.g., 10 times) in total. And further such procedure is sequentially repeated in the longitudinal direction of the product 10. It is possible to perform a simultaneous parallel operation of executing a transverse inspection of a certain portion of the product while executing a transverse inspection of another portion of the product by using another combination of the light source and the one-dimensional line sensor.

Upon completion of inspecting the product of a desired length (i.e., after plural transverse inspections of the product) or upon completion of one transverse inspection of the product, a required process is executed by the image data processing means 40 on the basis of the image data obtained at each of the incidence angles and stored in the memory of the image data processing means 40 as in the aforementioned first embodiment, whereby any defect in the product is detected.

It is to be noted that the optical sensor may consist of a two-dimensional line sensor instead of a plurality of one-dimensional line sensors. The automatic image scanning method in such a case can be carried out in the same manner fundamentally as the foregoing method described in connection with the third embodiment.

Although the present invention has been described hereinabove with reference to the preferred embodiments thereof, it is to be understood that the present invention is not limited to such embodiments alone. For example, if the optical sensor 30 employed in the first and second embodiments has a sufficient length, it may be held fixedly as well. And the incidence angle varying means in the first and second embodiments may be formed into any other adequate type. For example, in a modification where the light source 20 is held fixedly and is equipped with a louver, the incidence angle of its light output upon the light transmission regions of the product can be varied by changing the angle of the louver. In another modification, a mirror may be disposed between the light source and the product in such a manner as to be rotatable for varying the incidence angle.

In the embodiments mentioned, the product taken as an example to be inspected is an aperture grille which is a color selecting mechanism employed in a cathode-ray tube. However, the automatic image scanning method of the present invention can be applied further to any product having zigzag-arrayed light transmission regions or various patterns including lines and spaces formed on a light transmission carrier such as a film.

Thus, according to the present invention, it becomes possible to achieve high-precision inspection of a product to consequently attain a desired contour in the light transmission regions of the product or a desired sectional shape thereof rapidly with high accuracy and remarkable facility.

What is claimed is:

1. An image scanning method for automatically inspecting a product having light transmission regions, comprising the steps of:

disposing a light source on one side of said product, while disposing an optical sensor on the other side of said product;

sequentially varying the incidence angle of a light output emitted from said light source and caused to be incident upon a plurality of the light transmission regions of said product simultaneously at each angle;

receiving, by said optical sensor, the light transmitted through the light transmission regions of said product at each of the varied incidence angles, thereby acquiring image data at each of said incidence angles with regard to said product;

obtaining a composite image data from the image data acquired at each of said incidence angles;

differentiating light distribution intensities in said composite image data to recognize the edges of the light transmission regions; and detecting any defect of said product on the basis of an examination of said edges of the light transmission regions.

2. The image scanning method according to claim 1, wherein said light source is displaced relatively to the light transmission regions of said product for varying the incidence angle of the light output emitted from said light source to the light transmission regions of said product.

3. The image scanning method according to claim 2, wherein said optical sensor is displaced in compliance with the relative displacement of said light source to the light transmission regions of said product.

4. The image scanning method according to claim 1, 2 or 3, wherein said optical sensor consists of a single one-dimensional line sensor.

5. The image scanning method according to claim 1, 2 or 3, wherein said optical sensor consists of a plurality of one-dimensional line sensors.

6. The image scanning method according to claim 1, 2 or 3, wherein said optical sensor consists of a two-dimensional line sensor.

7. An image scanning apparatus for automatically inspecting a product having light transmission regions, comprising:

a light source disposed on one side of said product;

an optical sensor disposed on the other side of said product;

an incidence angle varying means for sequentially varying the incidence angle of a light output emitted from said light source to a plurality of the light transmission regions of said product simultaneously at each angle; and an image data processing means for processing the image data obtained with regard to said product by said optical sensor which receives the light transmitted through the light transmission regions of said product at each of the varied incidence angles.

8. The image scanning apparatus according to claim 7, wherein said incidence angle varying means is a light source moving mechanism which displaces said light source relatively to the light transmission regions of said product.

9. The image scanning apparatus according to claim 8, wherein a sensor moving mechanism is provided for displacing said optical sensor in compliance with the relative displacement of said light source to the light transmission regions of said product.

10. An image scanning apparatus for automatically inspecting a product having light transmission regions, comprising:

a plurality of light sources disposed on one side of said product and emitting light outputs therefrom at mutually different incidence angles to a plurality of the light transmission regions of said product simultaneously;

an optical sensor disposed on the other side of said product; and an image data processing means for processing the image data obtained with regard to said product by said optical sensor which receives the light transmitted through the light transmission regions of said product at each of said different incidence angles, obtains a composite image data from the image data acquired at each of said incidence angles, differentiates light distribution intensities in said composite image data to recognize the edges of the light transmission regions, and detects any defect in said product on the basis of an examination of said edges of the light transmission regions.

11. The image scanning apparatus according to any of claims 7 to 10, wherein said optical sensor consists of a single one-dimensional line sensor.

12. The image scanning apparatus according to any of claims 7 to 10, wherein said optical sensor consists of a plurality of one-dimensional line sensors.

13. The image scanning apparatus according to any of claims 7 to 10, wherein said optical sensor consists of a two-dimensional line sensor.

* * * * *